US005863715A

United States Patent [19]

Rajotte et al.

[11] Patent Number: 5,863,715

[45] Date of Patent: Jan. 26, 1999

[54] METHODS FOR BULK CRYOPRESERVATION ENCAPSULATED ISLETS

[75] Inventors: Ray V. Rajotte; Jonathan R.T. Lakey, both of Edmonton, Canada; C. Budd Colby, Los Altos Hills; Michael Flashner, Danville, both of Calif.; Garth L. Warnock, Edmonton, Canada

[73] Assignee: The Governors of the University of Alberta, Canada

[21] Appl. No.: 587,877

[22] Filed: Jan. 11, 1996

Related U.S. Application Data

[63] Continuation-in-part of Ser. No. 372,174, Jan. 12, 1995, abandoned.

[51] Int. Cl.[6] .......... A01N 1/02

[52] U.S. Cl. .......... 435/1.3; 165/263

[58] Field of Search .......... 435/1.3, 2; 165/263

[56] References Cited

U.S. PATENT DOCUMENTS

| | | | |
|---|---|---|---|
| 3,943,770 | 3/1976 | McDonald . | |
| 4,117,881 | 10/1978 | Williams et al. . | |
| 4,194,369 | 3/1980 | Faust et al. . | |
| 4,251,995 | 2/1981 | Pert et al. | 62/60 |
| 4,327,799 | 5/1982 | Scheiwe et al. . | |
| 4,352,883 | 10/1982 | Lim | 435/178 |
| 4,386,895 | 6/1983 | Sodickson | 425/5 |
| 4,469,227 | 9/1984 | Faust . | |
| 4,565,073 | 1/1986 | Lavender . | |
| 4,675,140 | 6/1987 | Sparks | 264/4.3 |
| 4,692,284 | 9/1987 | Braden | 264/4.3 |
| 4,764,463 | 8/1988 | Mason | 424/101 |
| 4,789,550 | 12/1988 | Hommel et al. | 424/493 |
| 4,814,274 | 3/1989 | Shioya et al. | 435/174 |
| 4,956,128 | 9/1990 | Hommel et al. | 264/4 |
| 4,965,186 | 10/1990 | Grischenko et al. | 435/2 |
| 5,017,338 | 5/1991 | Surgenor . | |
| 5,071,741 | 12/1991 | Brockbank | 435/2 |
| 5,175,093 | 12/1992 | Seifert | 435/41 |
| 5,192,553 | 3/1993 | Boyse et al. | 435/529 |
| 5,364,756 | 11/1994 | Livesey et al. | 435/2 |

FOREIGN PATENT DOCUMENTS

| | | |
|---|---|---|
| 0564 880 A1 | 1/1990 | European Pat. Off. . |
| WO 91/07951 | 6/1991 | WIPO . |
| WO 93/24076 | 12/1993 | WIPO . |
| WO 93/24077 | 12/1993 | WIPO . |

OTHER PUBLICATIONS

Rajotte, R.V. et al., "Pancreatic Islet Banking the Transplantation of Frozen Thawed Rat Islets Transported Between Centers," Abstract, AN 82:183249 *BIOSIS*.

Rajotte, R.V. et al., "Pancreatic Islet Banking the Transplantation of Frozen Thawed Rat Islets Transported Between Centers," *Cryobiology*, 18:357–369 (1981).

Brendel et al., "Improved functional survival of human islets of langerhans in three–dimensional matrix culture," *Cell Transplantation*, 3(5):427–435 (1994).

Chao et al., "Entrapment of cultured pancreas islets in three–dimensional collagen matrices," *Cell Transplantation*, 1:51–60 (1992).

Coulombe et al., "Prolongation of islet xenograft survival by cryopreservation," *Diabetes*, 36(9):1086–1088 (1987).

Evans et al., "Reversal of diabetes in dogs by transplantation of pure cryopreserved islets," *Transplantation*, 50(2):202–206 (1990).

Lacy et al., "Perifusion of isolated rat islets in vitro—Participation of the microtubular system inthe biphasic release of insulin," *Diabetes*, 21:987–998 (1972).

Lakey et al., "Development of a method for bulk cryopreservation of purified canine islets and human pancreatic microfragments," *Cell Transplantation*, 3:213 (1994).

Ohgawara et al., "Maintenance of embedded pig pancreatic pseudo–islets in a collagen gel matrix: study of the effect of hydrocortisone, a collagenase inhibitor, and nicotinamide on collagenolysis and the morphogenesis of pancreatic islet–cells in collagen gel matrix," *In Vitro Cell. Dev. Biol.*, 26:348–352 (1990).

Rajotte et al., "Islet isolation and cryopreservation in rats and dogs," *Diabetes Mellitus*, pp. 218–228 (1990).

Rajotte et al., "Viability studies on frozen–thawed rat islets of langerhans," *Cryobiology*, 14:116–120 (1977).

Rajotte et al., "Feasibility of low temperature banking for pancreatic islet cell transplantation," *Islet Isolation, Culture and Cryopreservation*, pp. 124–133 (1981).

(List continued on next page.)

*Primary Examiner*—Sandra E. Saucier

*Attorney, Agent, or Firm*—Townsend and Townsend and Crew LLP

[57] ABSTRACT

A method for bulk cryopreservation of biological material includes the steps of providing a flexible container, such as a freezer bag, containing biological material that is treated with a cryoprotectant and freezing the biological material to below −100° C. and preferably below −196° C. for deep freeze long-term storage. In the preferred embodiment, the bag is placed in a holder that maintains the cross-sectional area of the bag essentially constant and small enough (e.g., about 5 mm width to facilitate uniform heat transfer to and from all regions the bag. This facilitates uniform nucleation of the biological material after supercooling which enables controlled and uniform slow cooling through from about −7.5° C. to a temperature in the range of about −40° C. to −80° C., thereby maintaining the viability of the cells. The single freezer bag method facilitates cryopreservation of large amounts of material, such as entire preparations of isolated islets, as compared to conventional multiple tube cryopreservation protocols and yields similar or improved recovery. In addition, the single freezer bag method reduces the risk of cross-contamination, a problem when adding and withdrawing material form multiple tubes before, during and after the cryopreservation freeze-thaw cycle. The bag construction also reduces the risk of freezing medium (e.g., liquid nitrogen) seeping into the bag and causing the bag to burst when thawing the material. The present invention is directed, in particular, to the cryopreservation of encapsulated islets in a flexible container wherein the container thickness during freezing is maintained around 5 mm. The freezing may also be accomplished by supercooling the encapsulated islets and inducing ice nucleation.

8 Claims, 6 Drawing Sheets

OTHER PUBLICATIONS

Rajotte et al., "Transplantation of cryopreserved and fresh rat islets and canine pancreatic fragments: comparison of cryopreservation protocols," *Cryobiology,* 20:169–184 (1983).

Rajotte et al., "Cryopreservation of insulin–producing tissue in rats and dogs," *World J. Surg.,* 8:179–186 (1984).

Rajotte et al., "Islet cryopreservation for clinical trials," *Diab. Nutr. Metab.,* 5(1):63–68 (1992).

Rajotte et al., "Optimizing Cryopreservation of isolated islets," *Transplantation Proceedings,* 21(1):2638–2640 (1989).

Rajotte et al., "Methods of islet cryopreservation," *Pancreatic Islet Cell Transplantation,* pp. 124–131 (1992).

Ricordi et al., "Islet isolation assessment in man and large animals," *Acta Diabetol. Lat.,* 27:185–195 (1990).

10
2
16

10
18b
2
4
3a
8
6
28
26
28a
28b
18a
18c
22
3b
24
14
18d
16
12
20
24

METHODS FOR BULK CRYOPRESERVATION ENCAPSULATED ISLETS

CROSS-REFERENCE TO RELATED APPLICATIONS

The present application is a continuation-in-part of U.S. patent application Ser. No. 08/372,174, filed Jan. 12, 1995, now abandoned and incorporated herein by reference in its entirety for all purposes.

FIELD OF THE INVENTION

The present invention relates to cryopreservation of biological materials as well as uses thereof. More particularly, the invention relates to a method for bulk cryopreservation of biological materials such as tissue, islets and other cells, including encapsulated materials.

BACKGROUND OF THE INVENTION

Cryopreservation has been an effective method for long-term storage of biological material such as islets. Long-term storage of cells and tissue for use in clinical transplantation is based on the inherent need to collect adequate donor cells or tissue and to have this available at times that are suitable for transplantation into a patient. For example, since current methods to isolate and purify sufficient numbers of islets of Langerhans from a human pancreas are limited and multiple donors are required for successful reversal of insulin-dependent diabetes mellitus, long-term storage allows the collection of adequate quantities of islets for subsequent transplantation. Also, with long-term storage, the recipient pool can be extended to include patients in other medical centers.

Current islet cryopreservation protocols generally are based on protocols originally developed for the cryopreservation of rodent islets. See Rajotte et al., "Viability Studies on Frozen-Thawed Rat Islets of Langerhans," *Cryobiology*, 14:116–120 (1977) (which is hereby incorporated herein by reference). These protocols use multiple glass freezing tubes and aliquot small quantities of islets per individual glass freezing tube. When these freeze-thaw protocols are expanded to large animals and humans, greater numbers of freezing tubes are needed to accommodate the increased number of islets being frozen. This may amount to 30–40 tubes for a typical human islet isolation. Also, the cryopreservation of large numbers of freezing tubes is labor-intensive and has an increased potential for microbial contamination. In addition, seepage of liquid nitrogen into the glass tubes during low-temperature storage is a potential hazard since the tubes most likely will explode if thawed without expelling the liquid nitrogen.

Thus, there is a need to provide a more effective method for cryopreservation of biological material in bulk (e.g., entire preparations of isolated islets) efficiently and with minimal risk of contamination or loss.

There is also a need to provide a more effective method for stabilizing, storing, and retaining the viability of biological material for transplantation, since multiple donors are usually required for the collection of materials, such as islets in adequate quantities. Collecting these materials over time requires proper storage and then culturing; therefore, improvements in the processes are needed whereby the viability of the materials is retained.

SUMMARY OF THE INVENTION

The present invention is directed to a method for cryopreservation of biological material that avoids the problems and disadvantages of the prior art. The method of the present invention includes the following steps: (1) providing a flexible container containing a solution of biological material and cryoprotectant; (2) reducing the temperature of the biological material to or below about −100°; and (3) maintaining essentially uniform heat transfer from all regions of the material throughout step (2). The uniform heat transfer facilitates freezing all of the biological material. The solution is then ready for low-temperature long-term storage. The single freezer bag method facilitates cryopreservation of large amounts of material, such as entire preparations of isolated islets, as compared to conventional multiple tube cryopreservation protocols with similar or improved recovery. In addition, the single freezer bag method reduces the risk of microbial contamination, a problem when adding and removing material from multiple tubes before, during and after the cryopreservation freeze-thaw cycle. The sealed bag construction also reduces the risk of storage liquid (e.g., liquid nitrogen) seeping into the bag and causing the bag to burst when thawing the material.

In the preferred embodiment, the bag is placed in a holder that maintains the cross-sectional area of the bag essentially constant and small enough to facilitate uniform heat transfer to and from all regions of the bag. This facilitates uniform nucleation of the biological material after supercooling which enables controlled slow cooling through the slow cooling phase, thereby maintaining the viability of the cells.

The present invention also is directed to encapsulation of the biological material before cryopreservation. Encapsulation is especially important when freezing fragile cells, such as pig islets, which may fall apart during cryopreservation unless they are first encapsulated. Typically, the islets or individual cells of the biological material are suspended in an aqueous solution of a reversibly gelable material, such as agarose or alginate.

Also provided by the present invention are methods for stabilizing cells such that they can be more easily shipped and then stored for longer periods of time through encapsulation. It is also part of the present invention that encapsulated cells increase the longevity and viability of the cells for transplantation. For example, fewer encapsulated islets are required to maintain the same level of plasma glucose in transplanted diabetic animals as unencapsulated or naked islets.

Further provided are particular bags and holders for use in cryopreservation. In particular, the bags or flexible containers have two laterally spaced separate and detachable compartments, which provide an auxiliary cryopreservation storage unit that can be used for viability testing. The holder promotes uniform heat transfer or uniform extraction of heat from the flexible container. The holder comprises two substantially planar panels and means for holding these panels at a substantially uniform separation wherein the flexible container is placed within these panels, allowing for substantially uniform heat transfer.

The above is a brief description of some deficiencies in the prior art and advantages of the present invention. Other features, advantages and embodiments of the invention will be apparent to those skilled in the art from the following description, accompanying drawings and appended claims.

DESCRIPTION OF THE PREFERRED EMBODIMENT

The term cryoprotectant is used in this specification. The following definition is provided to aid disclosure, rather than to limit the invention. The term "cryoprotectant" refers to an agent that prevents biological damage during freezing by inhibiting formation of ice crystals, as well as minimizing osmotic stress to the cells and tissues.

Figure 1:
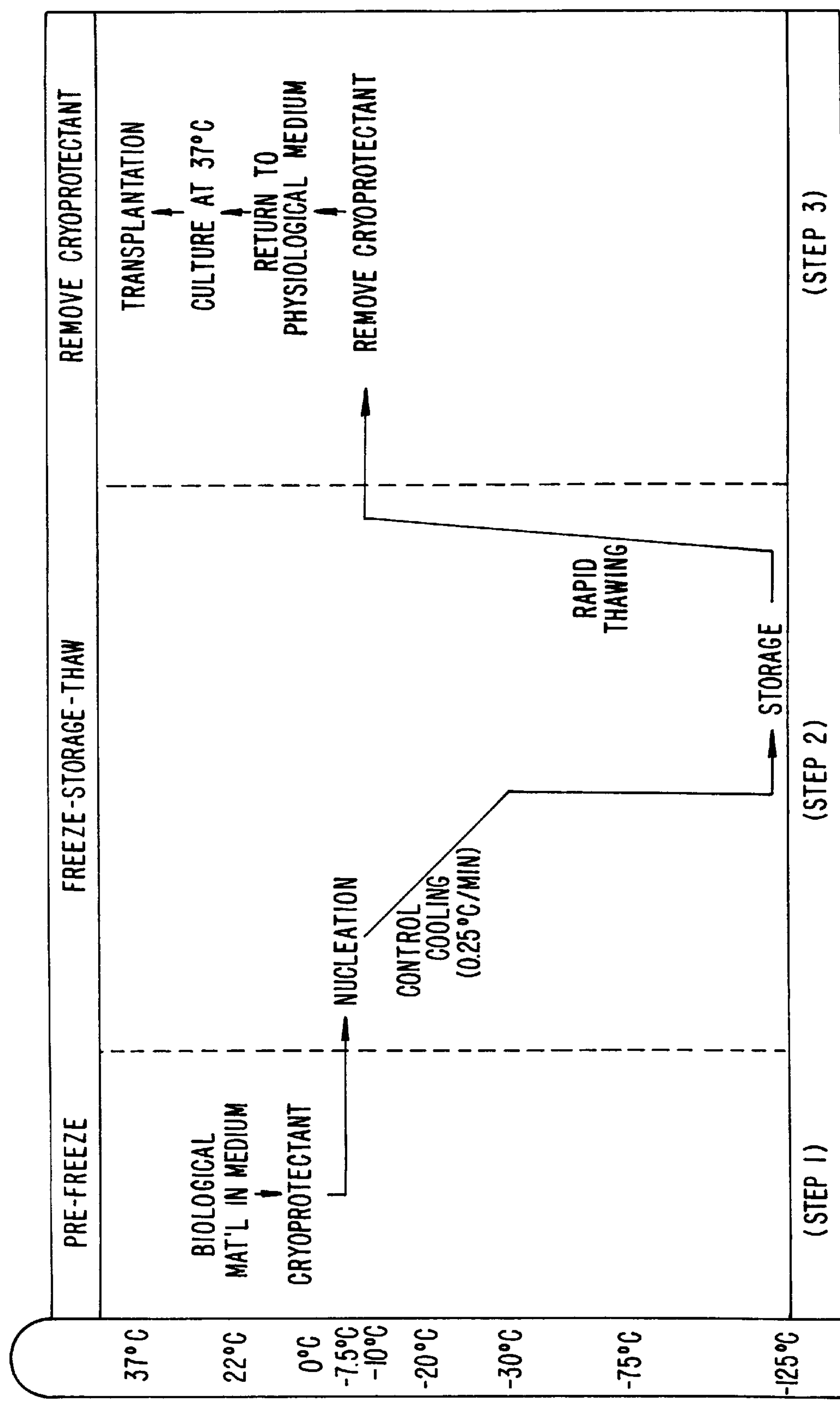
FIG. 1 is a diagrammatic representation of the basic steps of cryopreservation protocols.

Cryopreservation and subsequent recovery of biological material, generally involves three steps. Referring to FIG. 1, these steps include: (1) adding a cryoprotectant to a solution containing the biological material to be cryopreserved; (2) cooling the solution of step 1 to a preselected temperature for storage; and (3) after thawing the mass produced in step 2, removing the cryoprotectant by using a sucrose or slow step dilution.

According to the present invention, which involves bulk cryopreservation, cryoprotectant, preferably dimethyl sulfoxide (DMSO), is added to biological material of interest (hereinafter "sample"), such as islets of Langerhans. The islets are suspended in a tissue culture medium, like Medium 199 (Gibco, catalogue #12340-022, Burlington, ON), supplemented with serum and antibiotic as would be apparent to one of ordinary skill. After the cryoprotectant becomes equilibrated with the cells, the mixture is supercooled to about −7.5° C., and then nucleated. Time is allowed for release of latent heat of fusion so that the entire mixture is completely frozen throughout. Then the frozen mass is slowly cooled at about 0.25° C./min to an intermediate temperature in the range of about −40° to −80° C. Once the mixture reaches this temperature, it is rapidly cooled to a temperature at which biological activity is very slow, which is generally below −100° C. and preferably around −196° C. To rapidly cool the sample from the intermediate temperature to the storage temperature, e.g., −96° C., the sample is plunged into liquid nitrogen which quickly freezes the sample for storage. When cryopreserved material is needed, it is retrieved from storage and rapidly thawed, e.g., at about 150° C. to 200° C./min 0° C., and then placed in an ice slush. The cryoprotectant is then removed either by sucrose or slow step dilution before being transferred to isotonic media and readied for in vitro viability testing or transplantation.

In carrying out the method of the present invention, the sample is placed in a container or plastic bag, which preferably is flexible, e.g., a freezer bag, capable of withstanding temperature changes from about 40° C. to −200° C. and, thus, capable of withstanding the variation in temperature during cryopreservation. One suitable type of freezer bag is commercially available from Baxter Healthcare Corporation, Fenwal Division, Deerfield, Ill., 60015, USA, under the name Cryocyte freezer bag. Although a wide range of container or bag sizes can be used, the invention will be described with reference to a 500 mL bag for purposes of example and without intent to limit the invention. However, the container or plastic bag can range in capacity from about 50 mL to about 500 mL. Typically, the capacity of the container or bag will be at least about 50 mL.

Figures 2, 3:
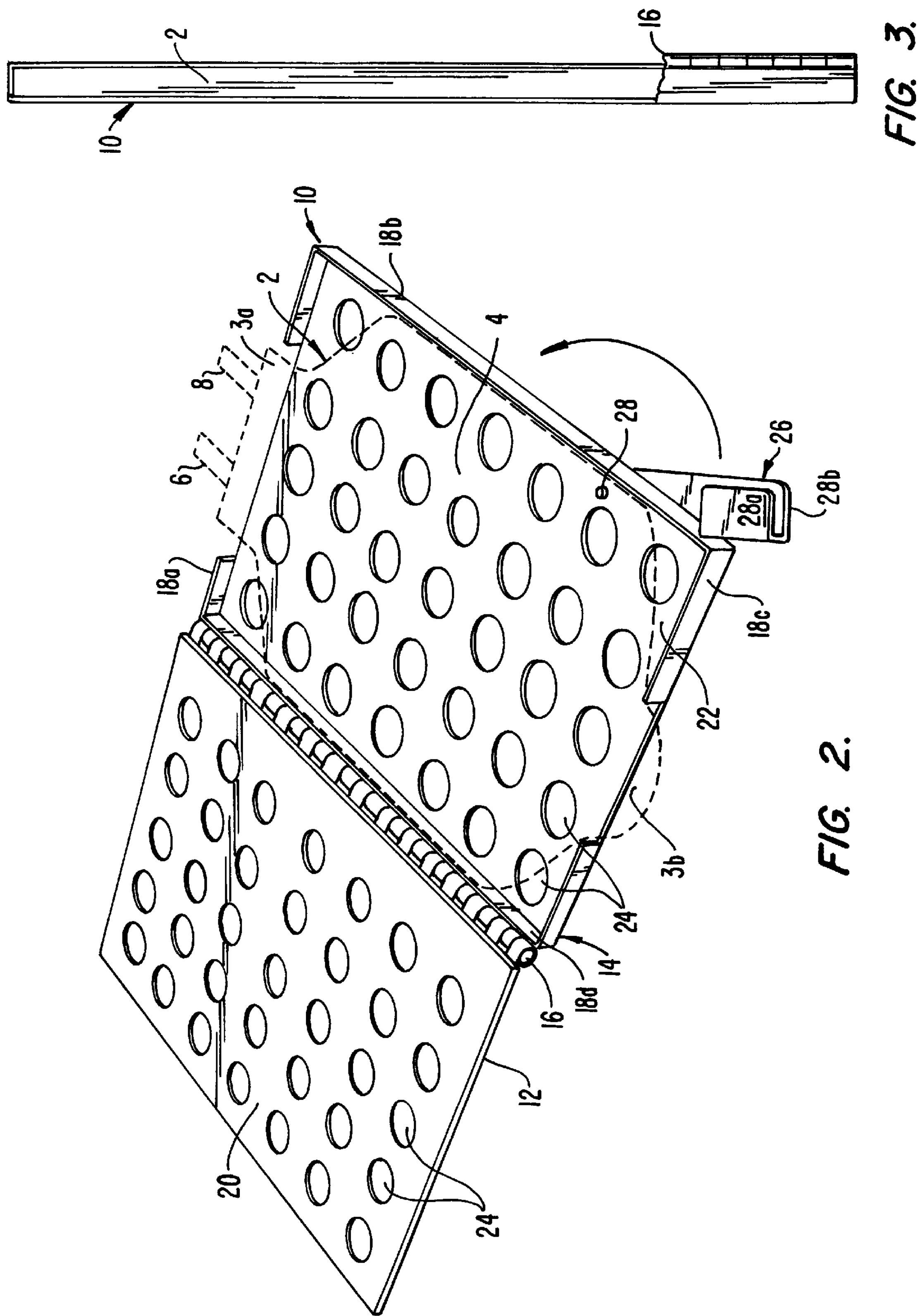
FIG. 2 is a perspective view of a cryopreservation bag and bag holder constructed according to the present invention and showing the holder in the open position.
FIG. 3 is a cross-sectional view of the holder of FIG. 2 in the closed position.
Figure 6:
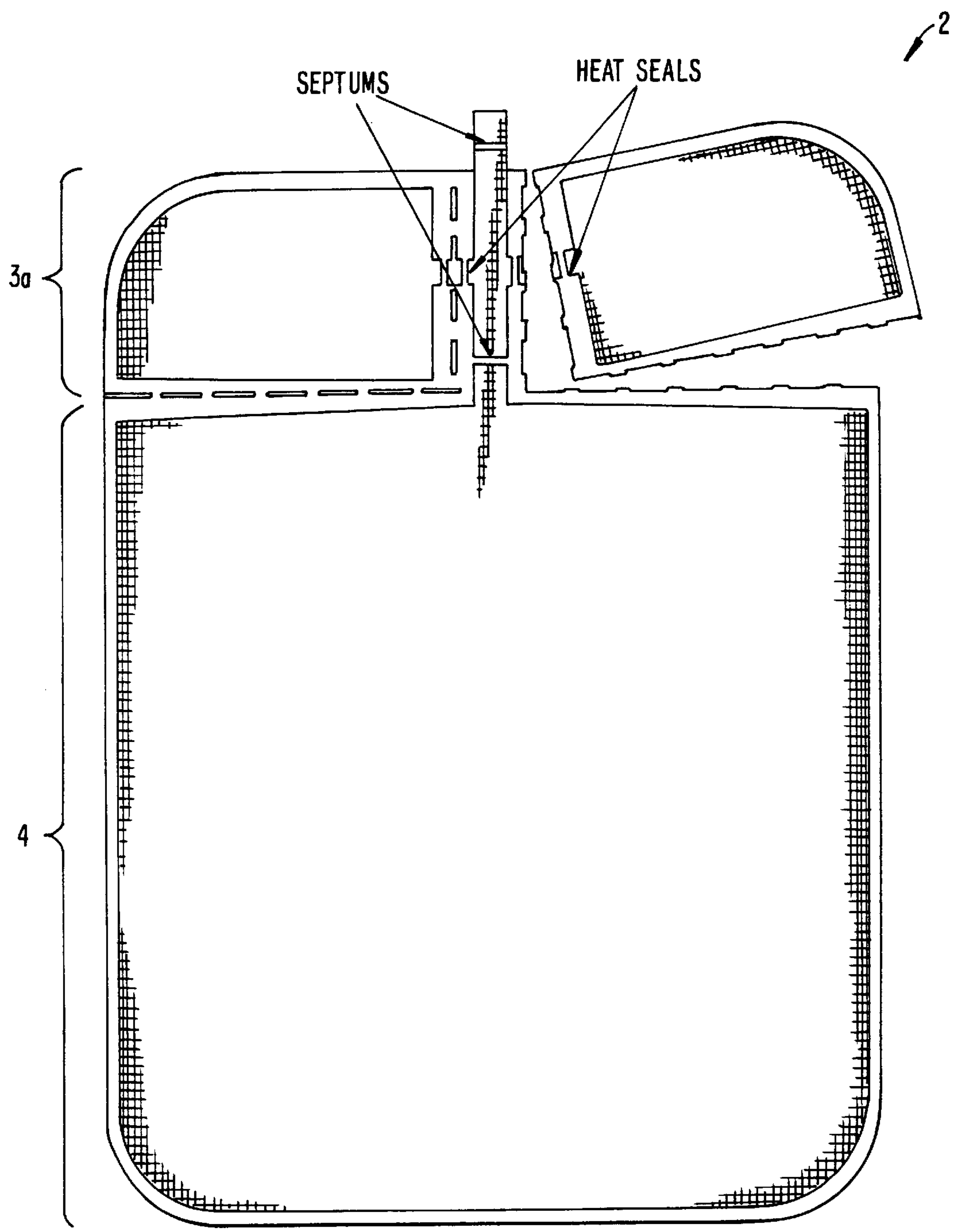
FIG. 6 shows the drawing of a prototype freezer bag that has two small compartments in which a small sample can be expelled for viability and/or sterility assessment.

It is important that heat transfer to and from essentially all regions within the freezer bag during freezing or thawing be maintained essentially uniform in order to minimize thermogradients and, thus, ensure uniform and controlled cooling from room temperature to 4° C., from 4° C. to −7.5° C., from −7.50° to the intermediate temperature (e.g., −40° C.), from the intermediate temperature to −196° C., and uniform, controlled thawing from −196° C. Referring to FIGS. 2 and 3, a freezer bag and holder assembly for facilitating uniform heat transfer to and from all regions of the material placed in the bag is shown according to the present invention. Referring to FIG. 2, freezer bag 2 includes a main chamber portion 4, an upper portion **3*a*, which includes inlet and outlet ports 6 and 8 through which material can be transferred into and out of main chamber portion 4, and a conventional lower tab portion 3*b* for hanging the bag. Ports 6 and 8 are provided with closure mechanisms or caps (not shown) as is conventional in the art. It is also contemplated to provide bag 2 (FIG. 6) with a pair of laterally spaced small compartments each depending from upper portion 3*a*. Each small compartment provides an auxiliary cryopreservation storage unit that can be used for viability testing and as an indicator of the viability of the material in main chamber portion 4. The freezer bag is specifically designed to allow known volumes of the preparation of tissue to be refluxed back from the main freezer bag into the two smaller side compartments. Two septa will be placed in the tubing. One is placed above the tubing entering the side ports and the other is placed below. Tubing containing a spike is placed through both septa when loading solution into the main freezer bag. When solution containing the islets or material is to be loaded into the side compartments the spike is partially removed to allow the tissue to be refluxed back into the side compartments. After loading of the tissue to the side compartments is complete the spike can be removed and the tubing which connects the main freezer bag to the side bags can then be sealed off. The side bags can be removed for microbiological and viability testing while the remainder of the preparation remains cryopreserved. The freezer bag is positioned in holder 10** which will be described in detail below.

Figure 4:
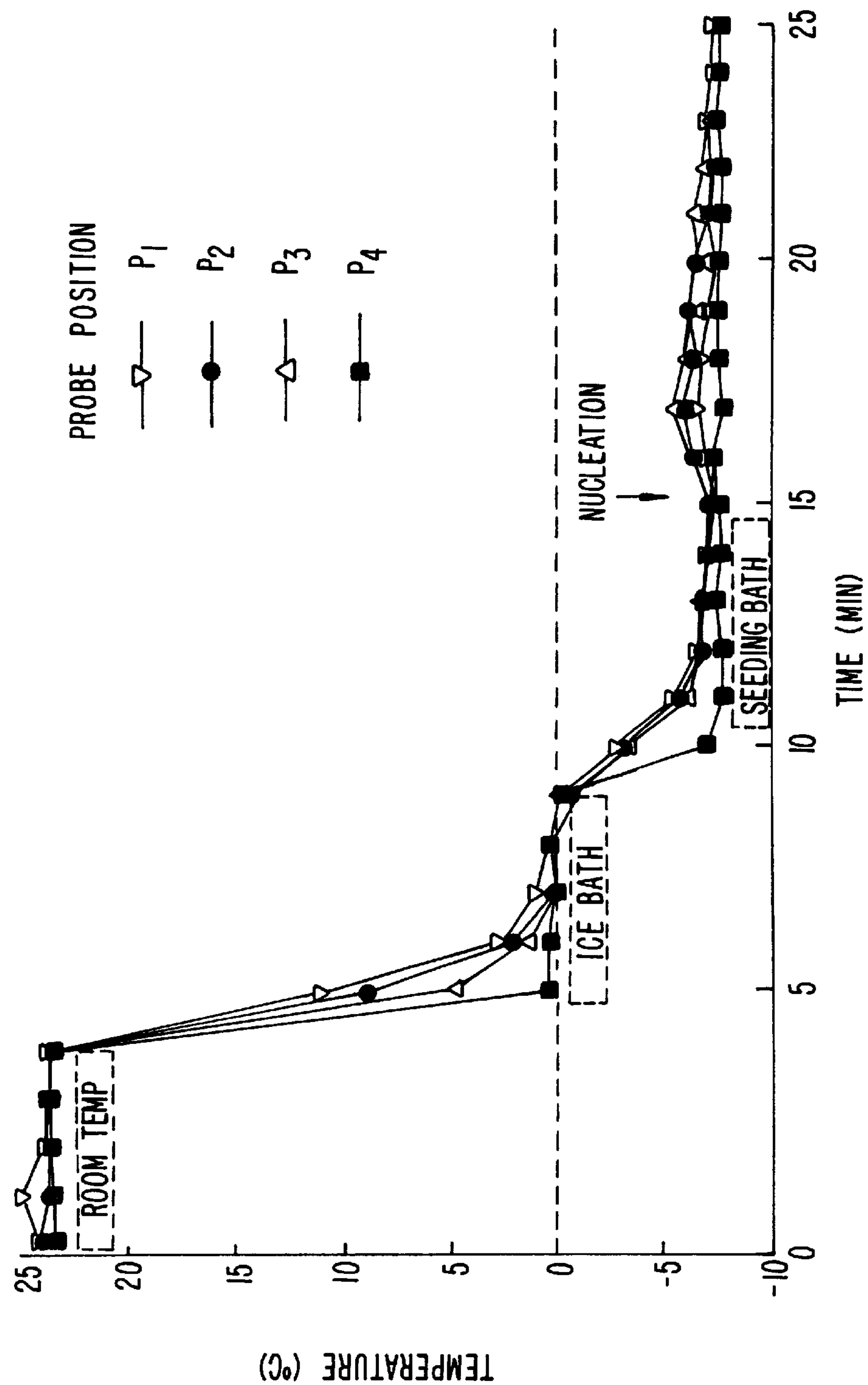
FIG. 4 shows four temperature profiles of biological material cooled through the release of the latent heat of fusion where the mass becomes frozen. The profiles illustrate essentially uniform heat transfer and temperature reduction throughout the mass. Three profiles were obtained from three thermocouples or probes ($P_1$, $P_2$, and $P_3$) distributed in the mass of biological material which was disposed in a freezer bag and holder assembly constructed in accordance with the bag and holder illustrated in FIGS. 2 and 3. The fourth profile (the compare profile) was obtained from a thermocouple or probe ($P_4$) positioned on the outside of the bag.
Figure 5:
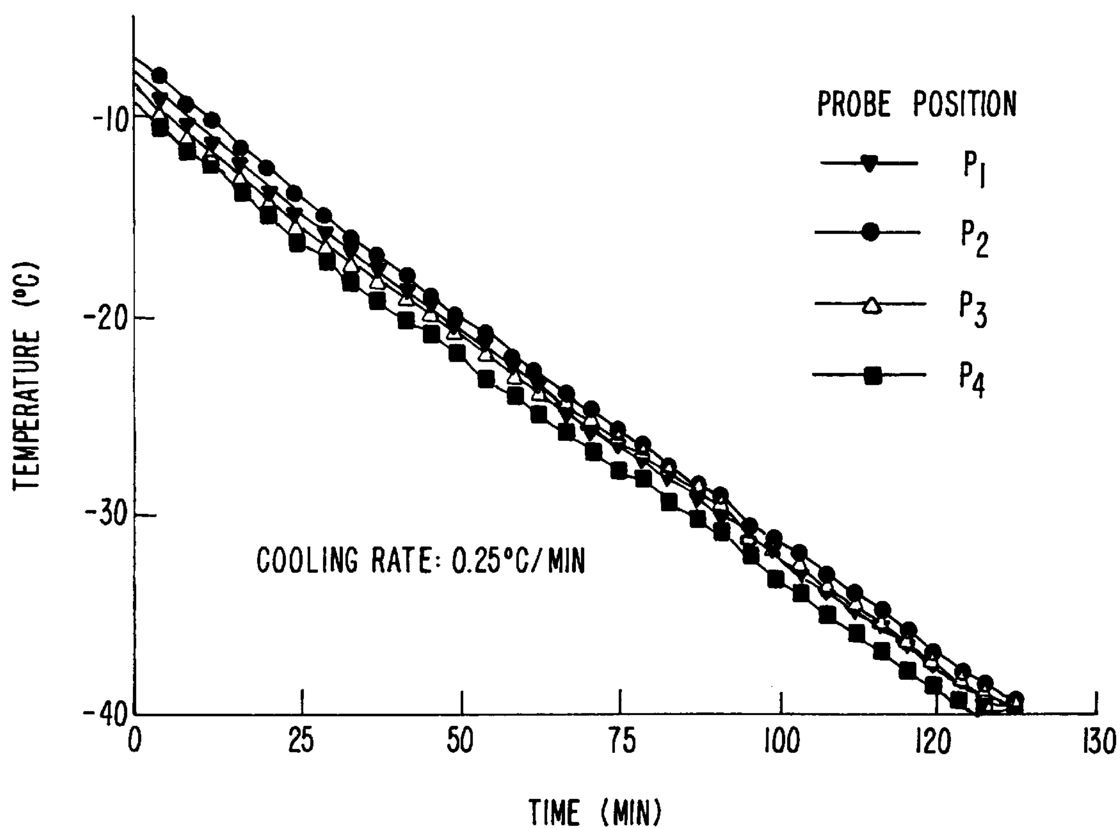
FIG. 5 shows the continuation of the temperature profiles of FIG. 4 for the same probes through the slow cooling phase of cryopreservation down to about −40° C. illustrating the controlled and uniform temperature reduction throughout the mass of biological material in accordance with the present invention. (The cooling rate was about 0.25° C. per minute.)

Holder 10 includes front panel 12 and rear panel 14 which are pivotally coupled to one another through hinge 16. Rear panel 14 includes side walls **18*a*, 18*b*, 18*c* and 18*d*. Side walls 18*a* and 18*c* include openings so that the portions 3*a* and 3*b* of bag 2 can extend therethrough. Sides 18*a–d* also are configured to engage front panel 12 such that essentially planar inner faces 20 and 22 of the front and rear panels, respectively, are maintained essentially parallel when the panels are positioned in the closed position as shown from a side view in FIG. 3. In this manner, the front and rear walls of bag 2, which preferably have uniform thickness for uniform heat transfer therethrough, remain essentially parallel so that the thickness of the bag remains uniform or constant when the bag is filled and secured within holder 10, independent of the fluid temperature within bag 2 or its orientation. The height of side walls 18***a–d* also is selected according to bag size to achieve uniform bag thickness. The uniform bag thickness facilitates uniform heat transfer to and from all regions of the solution placed in the bag as shown in FIGS. 4–5. In the preferred embodiment, holder 10 is constructed to maintain a uniform bag thickness of about 5 mm±10%. In order to ensure that the bag can conform to the holder configuration and have a generally flat shape of uniform thickness when filled, when a flexible bag is used, the bag preferably is only partially filled. For example, a 500 mL capacity bag is preferably filled with about 100 mL of solution comprising the sample and the cryoprotectant. If filled to capacity, for example, the side walls of the bag would bulge, thereby rendering the bag thickness nonuniform.

A plurality of uniformly distributed openings 24 are formed in panels 12 and 14 to provide direct contact between a substantial portion of the front and rear walls of the bag and the cooling medium to enhance heat transfer to and from the bag. The uniform distribution of holes also enhances maintaining uniform heat transfer within the bag during the cooling and heating phases. In addition, the holder preferably comprises material having high heat conductivity so that heat exchange between the bag and the environment can readily occur. Examples of suitable material include, e.g., aluminum, stainless steel and the like, with stainless steel being preferred.

Holder 10 also includes latch 26, which is provided to secure the panels together and maintain holder 10 in the closed position. Latch 26 is illustrated as being pivotally coupled to panel 22 through pin 28, but can be coupled to panel 12 in the alternative. To secure holder 10 in the closed position, panels 12 and 14 are pivoted to face one another. Then, latch 26 is pivoted in the direction of arrow 28 so that spaced arms 28*a* and 28*b* of the latch engage panels 12 and 14. Although a particular latch has been described, other mechanisms can be used to secure holder 10 in the closed position, such as hook latches, clamping latches, external clamps, etc. In addition, although a particular holder configuration has been described to facilitate essentially uniform heat transfer from all regions of the bag, holders that maintain the bag in other configurations suitable for such uniform heat transfer also can be used.

FIGS. 4 and 5 illustrate the uniformity of cooling of 100 mL of 2M DMSO solution in a 500 mL freezer bag when enclosed within a holder constructed according to holder 10 as described above. The holder was fabricated from stainless steel. The temperature profiles in these figures were obtained from four temperature probes. The first probe was placed in the upper region of the bag, about ⅓ the way down from the top edge. The second probe was placed in the middle region of the bag. The third probe was placed in the lower region of the bag, about ⅓ the way up from the bottom edge of the bag. The fourth probe was placed on the outside of the bag to measure the ambient temperature, e.g., the cooling bath temperature when the bag was placed therein. The curves representing data from the first, second, third and fourth probes are designated with reference characters P1, $P_2$, $P_3$ and $P_4$, respectively.

As shown in FIGS. 4 and 5, the heat transfer was rapid with essentially uniform temperature reduction throughout all regions of the bag from initial cooling through supercooling to about −7.5° C. (FIG. 4) and throughout the slow cooling phase which was completed at about −40° C. (FIG. 5). Uniform temperature throughout all regions of the biological material during supercooling is critical to ensure that the sample is completely frozen for slow controlled cooling from −7.5° C. to an intermediate temperature that can range from about −40° C. to about −80° C. depending on the sample. Once the intermediate temperature is reached the sample is rapidly cooled to the storage temperature which is below about −100° C. and preferably below −196° C. for long-term storage. For islets, the sample can be rapidly cooled once it reaches −40° C. during the slow cool phase. Other materials may require slow cooling to about −80° C. before rapid cooling to provide the desired recovery. In any case, however, the slow cooling phase can be continued to −80° C. (to ensure minimal intracellular ice before rapid cooling). It is also noted that if a larger volume of solution were to be used in the freezer bag, for example, 200 mL, a larger equilibration period in the seeding bath would be required to ensure that the temperature of the solution in the freezer bag is reduced to that of the seeding bath prior to nucleation.

The bulk cryopreservation method of the present invention can be used for cryopreservation of a wide range of biological materials including, but not limited to, islets such as human islets of Langerhans, pig islets, and rat islets, as well as other cell types, such as hepatocytes, neuroendocrine cells, proliferating cells and cell lines that secrete hormones, cytokines, lymphokines and cell growth regulators. As would be apparent to one of ordinary skill in the art, these cells and tissue can be obtained from mammalian tissue, primary cultured cells, cultured cell lines producing biological products and genetically engineered cultured cell lines. The size of the bag and, thus, the quantity of cryogenically preserved material also can vary depending on the clinical application.

General Cryonreservation Methodology

The following illustrates the general method of the bulk cryopreservation method of the present invention in conjunction with canine islets. However, other materials, such as those described above, can be preserved using the same methodology discussed below.

A sample of canine islets suspended in tissue culture Medium 199, described above and containing 10% fetal calf serum and penicillin/streptomycin, is placed in a 500 mL bag at room temperature (about 22° C.). The cryoprotectant DMSO, which is made up in supplemented Medium 199, is added in a stepwise fashion into the freezer bag to a final concentration of between about 0.5 to about 2.0M. The bag, containing about 100 mL solution of the sample and Medium 199 in 2M DMSO, is placed in a holder, constructed in accordance with holder 10 as described above, and the holder is closed as shown in FIG. 3. The holder is stainless steel and is fabricated to maintain a uniform inner cross-sectional bag thickness of about 5 mm±10% throughout substantially the entire main portion of the bag. The bag and holder assembly is then transferred to an ice bath to reduce the temperature of the solution containing the samples culture medium and DMSO to about 0° C. Then, the bag and holder assembly is transferred to a seeding bath where the sample is allowed to supercool to about −7.5° C. Once the sample reaches −7.5° C., it is nucleated, for example, with ice crystals or a supercooled metal rod is placed against the side of the freezer bag, and time is allowed for the release of the latent heat of fusion from the solution comprising the sample and DMSO. Temperature profiles for the foregoing preparation, which was cooled as described above through supercooling, is shown in FIG. 4. The time allowed for the release of the latent heat of fusion is about 15–20 minutes. After the suspension is frozen, the bag and holder assembly is placed in a cooling apparatus, such as RT 209 Multicool bath manufactured by FTS Systems, Inc., Stone Ridge, New York fitted with a Rex-P90 temperature programmer, where the suspension is then further cooled, at 0.25° C./min to about −40° C. The temperature profiles for this phase of this example are shown in FIG. 5. Then the bag and holder assembly is plunged into liquid nitrogen, which is contained in a vessel, for rapid cooling down to about −196° C. where the material is stored. Once the bag has reached liquid nitrogen temperature, the holder is removed and the freezer bag is stored in a liquid nitrogen storage tank.

When the solution volume varies from that discussed in the foregoing example, the method is slightly varied as would be apparent to one of ordinary skill. More specifically, when the volume in the freezer bag is increased, a longer period of time is needed to supercool the 2M DMSO solution before nucleation is carried out. In addition, the duration of time for the release of the latent heat of fusion is extended to ensure that all the latent heat of fusion has been released prior to the slow cooling process.

When the frozen islets are needed for transplantation, one or more bags are removed from the liquid nitrogen storage vessel and thawed rapidly, i.e., at about 200° C./min. This can be accomplished by placing the bag in a water bath at about 40° C., for example. That is, when slow cooling at 0.25° C./min to about −40° C. is used, then rapid thawing from −196° C. is needed for maximal survival of the sample, which in this case is islets. However, if slow cooling at 0.25° C./min to about −80° C. is used, then slow or fast thawing from −196° C. can be used; however, slow thawing may be better for maximal survival as shown by Rajotte et al., "Optimizing Cryopreservation of Isolated Islets," Transplantation Proceedings Vol. 21, #1 (1989) pp. 2638–2640. To minimize osmotic stress to the islets, the DMSO is removed slowly once the temperature of the suspension reaches about 0° C. This can be accomplished by using either a sucrose dilution or a slow step dilution.

When a sucrose dilution is used, the freezer bag containing the thawed islets is taken from the water bath and drained into a siliconized 250 mL centrifuge tube and centrifuged. The supernatant is removed and 25 mL of 0.75M sucrose is added to the 250 mL centrifuge tube and the temperature is maintained at about 0° C. for about 30 minutes. The tube is gently mixed every 5 minutes to resuspend the islets. The sucrose is then diluted by adding 25 mL of supplemented Medium 199 in a stepwise fashion. These sucrose dilution steps are carried out at room temperature. Additional aliquots of Medium 199 solution, first 25 mL, then 50 mL and finally 100 mL are added to the tubes with 5 minutes allowed between each additional step. After the final addition of 100 mL of medium 199 solution, the tube is centrifuged and the supernatant is removed and replaced with tissue culture media containing 10% serum and penicillin/streptozotocin. The islets are then ready for in vivo transplantation.

Although a sucrose dilution method can be used, the slow step dilution has particular advantages. For example, the slow step dilution does not require centrifuging which can physically damage the sample and result in lower recovery. That is, the slow step dilution is less stressful to the islets. The slow step dilution involves adding physiological media to the bag containing the islets in 2M DMSO. As media is added to the bag, the concentration of the DMSO in the freezer bag decreases.

To make the process of adding and removing the cryoprotectant more standardized and simpler, a computer-controlled system can be used to add the cryoprotectant following a specific timed sequence, while keeping the suspension of tissue within the bag well mixed via a controlled agitator device which shakes the bag.

Using the bag and holder assembly cryopreservation method described above, cryopreservation of large quantities of biological material in a single container has been achieved with substantially similar or improved recovery as compared to conventional tube cryopreservation techniques, which may involve using 30–40 15 mL glass freezer tubes to store a similar amount of material. Moreover, biological material cryogenically preserved according to the method of the present invention is equally or better able to withstand prolonged storage without a significant reduction in viability.

The invention will be described in greater detail by way of specific examples. The following examples are offered for illustrative purposes, and are not intended to limit the invention in any manner. Specifically, the following examples are provided to illustrate some of the benefits described above.

EXAMPLE 1

Cryopreservation of Rat Islets

In this series of experiments, islet recovery was assessed after addition and removal of the cryoprotectant agent DMSO. In paired experiments, groups of 500 rat islets were aliquoted to either a single 500 mL freezer bag or 4 standard glass freezing tubes. The results indicated an essentially equal percent recovery of islets from either the freezer bag or the glass tubes (90±2.3 for tubes versus 92±4.8 for freezer bags). The significance of these experiments is that they demonstrate that the cryoprotectant DMSO can be safely added and removed from islets in the freezer bag with only a <8% loss in islet recovery. They demonstrate that the composition of the bag does not harm the islets.

EXAMPLE 2

Cryopreservation of Canine Islets

Known numbers of canine islets (5–8000 islet equivalents) were aliquoted into a first group of 6 glass tubes. Equivalent numbers of islets from the same isolation were allocated to a single 500 mL freezer bag. The islets were cryopreserved using the techniques described above including adding the cryoprotectant DMSO stepwise to a final concentration of 2M. The tubes and bag were then supercooled to −7.5° C. and nucleated with a supercooled metal rod. Before nucleation the bag was placed in a stainless steel holder corresponding in structure to holder 10 and configured to maintain an inside bag thickness of about 5 mm with the bag filled to about 100 mL. After allowing time for the release of the latent heat of fusion, each freezer bag was then slow-cooled at about 0.25° C./minute to about −40° C. The tubes were slow-cooled at the same rate. The tubes and bags were then plunged into liquid nitrogen for low-temperature storage. At this low temperature, the storage time is indefinite. After a period of storage of about 1–2 weeks at −196° C., the tubes and bags were rapidly thawed from −196° C., in a 40° C. water bath before the DMSO was slowly removed using a sucrose dilution. Frozen-thawed islets were counted and the percentage recovery was calculated from the pre- and post-freeze counts. The following table illustrates the recovery data from this experiment.

TABLE 1

| GROUPS | n (members in group) | Mean Recovery |
|---|---|---|
| Tubes | 7 | 76.7 ± 6.1 |
| Bags | 7 | 75.9 ± 11.3 |

As can be seen from the foregoing, the recovery ranges from the tubes and bags are essentially similar.

Prior to viability testing in perifusion, the remaining frozen-thawed canine islets were cultured at 37° C. for 48 hours in CMRL solution which had been supplemented with 10% Fetal Calf Serum, 25 mM HEPES and penicillin/streptomycin. In perifusion, known numbers of islets were exposed to low (50 mg/dL), and high (500 mg/dL) glucose solutions with the effluent collected for determination of insulin content.

Figure 7:
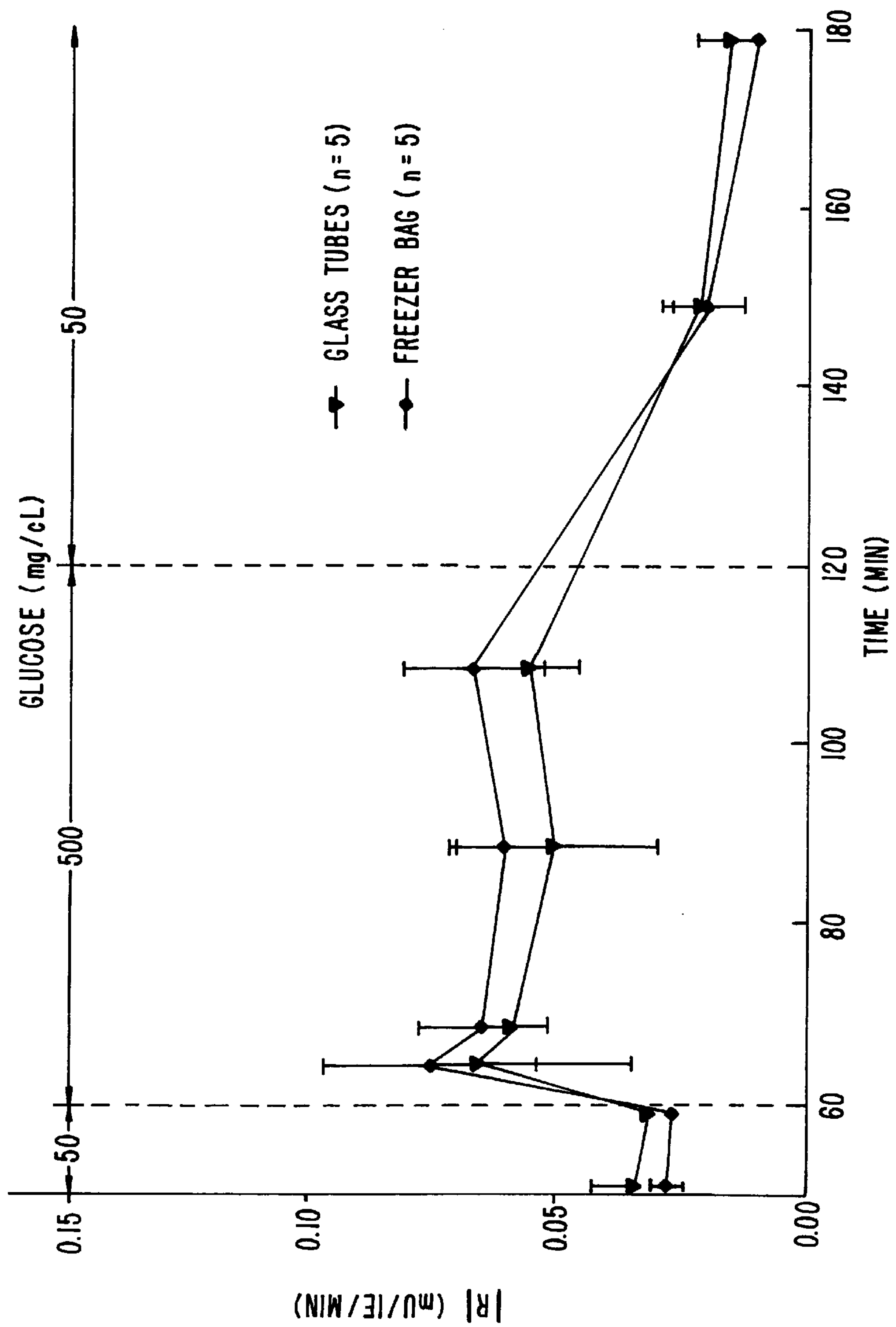
FIG. 7 illustrates the insulin secretion after glucose stimulation of canine islets, which were cryopreserved in either a single freezer bag: ♦ or in glass freezer tubes: ▼.

The functional response of the frozen-thawed canine islets, cryopreserved in either a single freezer bag or in 6 glass freezer tubes, is illustrated in FIG. 7. Islets from both groups show comparably low initial basal insulin secretion levels. Insulin secretion increases in both groups during the high glucose stimulatory phase. Islets from both groups show a typical biphasic pattern of insulin release which returns back to pre-stimulatory levels following cessation of the high glucose solution. The calculated stimulation index which compares the insulin secretion during high glucose to the insulin secretion during both phases of low glucose is comparable between the two experimental groups with a 2.7 fold increase observed in the islets cryopreserved in the freezer bag and a 2.0 fold increase in islets cryopreserved in the standard glass tube.

EXAMPLE 3

Cryopreservation of Unpurified Human Islets

Further experiments were performed using pancreatic tissue from unpurified human islet isolation. Unpurified islets containing human pancreatic microfragments from 10 multiorgan donors were cryogenically preserved. The following Table 2 illustrates data obtained from ten experiments. In each experiment, human pancreatic tissue was equally allocated into either a single freezer bag and holder system, as described above, or ten glass freezer tubes, and the material was cryogenically preserved for about 1–4 weeks. The islet tissue in the bags was cryogenically preserved using the bag protocol discussed above, while the islet tissue in the tubes was cryogenically preserved using conventional techniques. The recovery obtained in these experiments is illustrated in the following Table 2.

TABLE 2

| GROUPS | n (members in group) | Mean Recovery |
|---|---|---|
| Tubes* | 10 | 56.0 ± 10.9 |
| Bags | 10 | 61.7 ± 8.9 |

*tissue equally aliquoted into 6–12 tubes (<0.5 g tissue/tube)

As evident from the data in Table 2, these experiments resulted in improved recovery after cryopreservation with the freezer bag protocol (61.7±8.9%) as compared to conventional tube techniques (56±10.9%). In addition there was a purification of the preparation with a 33.2±5.5% decrease in the amylase concentration in unpurified human islets cryogenically preserved in the freezer bag and a 43.3±13% decrease in the tubes.

Encapsulated Material

In an alternative embodiment of the invention, the biological material is encapsulated before cryopreservation. The encapsulation step is especially important when freezing very fragile cells such as pig islets or islets that may be fragile after the isolation procedure or during culture, which, without encapsulation, typically fall apart during cryopreservation. Encapsulation also protects the architecture of the cell or tissue so that when subjected to physical trauma, for example, tissue culture viability is not significantly affected. In addition, encapsulation prior to cryopreservation avoids the need to provide encapsulation at a second site to which the frozen cells may be shipped.

Encapsulation of cells or biological material improves their physical stability, making them easier to cryopreserve, store, culture and/or ship between locations. The encapsulated materials are more metabolically effective, post-transplant, than are the unencapsulated materials, resulting in greater viability and function. Furthermore, encapsulated cells are more readily recovered from culture and/or after cryopreservation than are unencapsulated cells.

These encapsulated materials can be effectively used in transplantation. Typically, the number of unencapsulated islets utilized for transplantation is about 10,000 to about 30,000 islets per kilogram of body weight when administered intraperitoneal (ip). When encapsulated islets are utilized, however, fewer islets are required to achieve or maintain the same level of plasma glucose (post transplantation) as the unencapsulated islets.

Encapsulation is a process that generally involves encapsulating tissue or a suspension of cells so that the encapsulated tissue or cells remain viable within a protective membrane or coating. The membrane or coating is permeable to nutrients, ions, oxygen, and other materials needed both to maintain the tissue and to support its normal metabolic functions, but is impermeable to bacteria, lymphocytes, and large proteins of the type responsible for immunological reactions resulting in rejection. The following discussion of well-known encapsulation methodologies is provided to illustrate suitable encapsulation methods that can be used to encapsulate the biological material before cryopreservation according to the present invention. However, it should be understood that the present invention is not intended to be limited to cryogenically preserved material encapsulated according to the particular encapsulation methods described below, as those methods are provided merely for purposes of example.

Typically, living tissue or individual cells are suspended in an aqueous solution of a reversibly gelable material, such as sodium alginate, and droplets of this suspension are formed and allowed to fall into a gelling solution, such as calcium chloride. One example of this general process is disclosed in U.S. Pat. No. 4,352,883 to Lim, which is incorporated herein by reference. The temporary capsules so formed are then treated with a crosslinking polymer, such as polylysine and polyethyleneimine, to form an outer semi-permeable coating. The droplets are typically formed by feeding the alginate suspension to a first site where a mass of the liquid suspension accumulates. Then the mass of liquid suspension is agitated such that it is broken up into small droplets. Devices using vibration, centrifugal force, air currents and electrostatic charges have been used to agitate the liquid to generate the small droplets. See, e.g., U.S. Pat. Nos. 4,692,284 to Braden, 4,386,895 to Sodickson, 4,789,550 to Hommel et al., and 4,814,274 to Shioya et al. The disclosures of which are hereby incorporated herein.

Experiments were performed to obtain percent recovery data for encapsulated and nonencapsulated material cryogenically preserved in bulk according to the bulk cryopreservation methodologies described above.

EXAMPLE 4

Cryopreservation of Encapsulated Canine Islets

In particular, known numbers of canine islets were placed in a single 500 mL freezer bag or into 6 glass freezer tubes. In addition, known numbers of canine islets from the same isolation were encapsulated and divided into two groups; one to be cryopreserved in a single freezer bag and the other to be cryopreserved in 6 glass tubes. The canine islets were encapsulated using a electrostatic generator.

All islets were cryopreserved according to the methodologies described above. The data from these experiments is described in the following Table 3.

TABLE 3

ENCAPSULATED CANINE ISLET RECOVERY FOLLOWING CRYOPRESERVATION IN FREEZER BAG V. GLASS TUBES

| Cryo Method | n (members in group) | % Recovery |
|---|---|---|
| Bag | 6 | 89 ± 5 |
| Tube | 6 | 93 ± 13 |

Isolated islets from a canine pancreas were encapsulated using above-described techniques. Islets were then cryopreserved using the above described techniques. Following a period of storage at −196° C. the freezer bag and glass tubes were thawed using described techniques. The average percent recovery following cryopreservation was then calculated and is shown in Table 3. The average recovery of islets, which were encapsulated prior to cryopreservation, was 89±5% from the freezer bag group and 93±13% for encapsulated islets cryopreserved in the glass tubes.

EXAMPLE 5

Transplantation of Encapsulated and Unencapsulated Islets into Nude Mice

Remaining frozen/thawed islets were then transplanted into diabetic nude mice and the results of these transplants are shown in Table 4.

TABLE 4

TRANSPLANTATION OF CANINE ISLETS

| Graft | Txp Dose (IE) | n | Txp Site | Graft Survival (days) |
|---|---|---|---|---|
| Frozen/Thawed Islets | | | | |
| Unencap-Tube | 2000 | 6 | KC | 0, 16, >50x4 |
| Unencap-Bag | 2000 | 8 | KC | 0, 16, 22*, >50x5 |
| Frozen/Thawed Encapsulated Islets | | | | |
| Encap-Tube | 2000 | 6 | IP | >50x6 |
| Encap-Tube | 4000 | 3 | IP | >50x3 |
| Encap-Bag | 2000 | 6 | IP | 0, >50x5 |
| Encap-Bag | 4000 | 3 | IP | >50x3 |
| Fresh (from historic data) | | | | |
| Unencap | 2000 | 11 | KC | 0x2, >54x2, 48x2, 25x2, >18x3 |
| Encap | 2000 | 13 | IP | >54x2, 48x4, >34x3, 25x2, >18x2 |
| Encap | 4000 | 9 | IP | >54x2, >34x2, 25x3, 18x2 |

Untransplanted diabetic control survived for 10.7 ± 1.6 days (n = 6) after alloxan injection.

IE = Islet equivalent
> = Islet graft still functioning
* = Died while normoglycemic
KC = Kidney capsule
IP = Intraperitoneal txp
Encap = Encapsulated
Unencap = Unencapsulated The NOD mouse is an inbred strain of mice that lack a thymus and thus any T cells and serve as optimal recipients of islet tissue since they cannot mount an immune response to destroy the grafted tissue. Mice were rendered diabetic with a single intravenous injection of alloxan, a beta cell specific toxin. Two thousand (2,000) unencapsulated frozen-thawed islets transplanted into a pouch created in the kidney capsule (KC) failed to return the basal blood glucose levels back to normoglycemic levels. When 2000 or 4000 frozen/thawed islets which had been encapsulated prior to cryopreservation were transplanted intraperitoneally (IP) into diabetic nude mice, all but 1 of the animals returned to normoglycemic blood glucose levels ($n_{total}$=18). These animals remained normoglycemic throughout the follow-up period. Historical controls transplanting freshly isolated islets are also shown in Table 4 for comparative purposes. There was no difference in in vivo islet function from encapsulated islets which had been cryopreserved in either the glass tubes or in a single freezer bag. In Table 4, the graft survival results are provided with days listed first then times the number of transplants.

EXAMPLE 6

Survival of Encapsulated Versus Unencapsulated Islets

The 48 hours post-cryopreservation survival rate of the islets which had been encapsulated prior to cryopreservation was also higher as compared to islets which had not been encapsulated prior to cryopreservation (Table 5).

TABLE 5

SURVIVAL OF FROZEN/THAWED CANINE ISLETS

| | n (members in group) | Immediate Post-Thaw (% Recovery) | 48 Hrs. Post-Thaw Culture (% Recovery) |
|---|---|---|---|
| Unencapsulated | | | |
| Bag | 7 | 76.3 ± 10.8 | 63.4 ± 5.3 |
| Tube | 7 | 81.4 ± 4.0 | 70.9 ± 3.7 |
| Encapsulated | | | |
| Bag | 6 | 89.0 ± 5.0 | 85.9 ± 5.9 |
| Tube | 6 | 83.5 ± 13.3 | 72.2 ± 8.2 |

The recovery of islets after a period of 48 hours of tissue culture at 37° C. following cryopreservation was 63.4% for unencapsulated islets cryopreserved in the freezer bag and 70.9% for unencapsulated islets cryopreserved in the freezer tubes. For islets which had been encapsulated prior to cryopreservation the post thaw survival was higher with a 85.9 recovery for encapsulated islets which had been cryopreserved in a freezer bag and 72.2% for encapsulated islets cryopreserved in the glass tubes.

The recovery of porcine islets after a period of 24 hours of tissue culture at 37° C. following cryopreservation was 3% for unencapsulated islets cryopreserved in glass tubes. For porcine islets which had been encapsulated prior to cryopreservation in glass tubes, the post thaw survival was higher with a mean of 53.5% recovery.

TABLE 5A

| | n (members in group) | Immediate Post-Thaw Recovery % | 24 Hrs Post-Thaw Culture Recovery % |
|---|---|---|---|
| Unencapsulated | 1 | 26 | 3 |
| Encapsulated | 2 | 55.5 | 53.5 |

As evident in Table 3, Table 4, Table 5 and Table 5A there is an improved recovery after cryopreservation and better in vivo function of islets which have been encapsulated prior to cryopreservation.

EXAMPLE 7

Viability Comparison of Unencapsulated and Encapsulated Canine Islets in Nude Mice Unencapsulated or naked (NK) canine islets and canine islets encapsulated with either a single (SC) or double coat (DC) of alginate were transplanted into nude mice, and the results of these transplants are shown in Table 6. The unencapsulated or naked islets were transplanted (Tx) into a pouch created in the kidney capsule or intraperitoneally (IP).

TABLE 6

NAKED, SINGLE AND DOUBLE COATED CANINE ISLET GRAFTS IN NUDE MICE

| Graft | Tx Dose (IE) | n | Tx Site | Graft Survival (days of euglycemia) | Success (%) 30 day survival | >100 day survival |
|---|---|---|---|---|---|---|
| NK | 550 | 2 | kidney | 0x2 | 0 | 0 |
| NK | 1000 | 8 | kidney | 0x6, 2, 13 | 0 | 0 |
| NK | 2000 | 16 | kidney | 0x4, 71, 85, 114, 116x3, 117, 120, 133x2, 156x2, 177x2 | 77 | 67 |
| NK | 1500 | 3 | ip | 0x1, 1x1, 117x1 | 33 | 33 |
| NK | 2000 | 10 | ip | 0x8, 6x1, 116x1 | 10 | 10 |
| NK | 4000 | 8 | ip | 0x7, 37 | 13 | 0 |
| SC | 250 | 8 | ip | 0x2, 12, 38x2, 87, 122x2* | 50 | 13 |
| SC | 500 | 18 | ip | 0x3, 23, 50, 135, 137x4*, 150, 170x2, 184*, 217*, 262x2*, >291 | 78 | 72 |
| SC | 1000 | 18 | ip | 119, 136x3*, 137x5*, 140, 150, 177*, 182*, 184x4*, 223* | 100 | 93 |
| SC | 1500 | 6 | ip | 26x1**, 70x1, 112x1*, 141x3* | 100 | 80 |
| SC | 2000 | 22 | ip | 28**, 49**, 117x2*, 120x3*, 136x2*, 137x2*, 148*, 156x2, 184x4*, >251x2, 262x2* | 100 | 100 |
| SC | 4000 | 11 | ip | 104, 120x2*, 133x2*, 149x4, 156x2 | 100 | 100 |
| DC | 1500 | 3 | ip | 0x1, 3x1, 117x1 | 33 | 33 |
| DC | 2000 | 11 | ip | 0x3, 25, 40, 97, 115, 117x3, 133 | 64 | 46 |
| DC | 4000 | 6 | ip | 0x3, 68x1*, 128, 147 | 40 | 40 |

IE = islet equivalent,
NK = naked,
DC = double coated with SMPA by calcium chloride chelation.
*found dead while normoglycemic.
SC = single coated with MXG by strontium chloride chelation
> graft function is still ongoing.
**grafts were recovered.

As shown in Table 6, the percentages of graft survivability were greater for the encapsulated islets than for the unencapsulated islets.

EXAMPLE 8

Long-Term Culture of Unencapsulated and Encapsulated Canine Islets

Unencapsulated or naked canine islets (NK) and canine islets encapsulated with a single coat (SC) of alginate were cultured for a one-, two-, or three-week period. As indicated in Table 7, a greater percentage of the encapsulated cells were recovered from culture than naked cells, as detected by dithiazone staining. Furthermore, encapsulated cultured cells were superior in their ability to support diabetic animals following transplantation (See Table 8).

TABLE 7

Recovery of Encapsulated and Naked Canine Islets from Long-term Culture

| Culture Time | Grafts | n | Pre-culture (IE)* | Post-culture (IE)* | Recovery (%) |
|---|---|---|---|---|---|
| 1 week | Naked | 5 | 5694 ± 930 | 3704 ± 795 | 63.1 ± 5.3 |
| | Encapsulated | 6 | 4829 ± 728 | 4995 ± 815 | 103 ± 4.3 |
| 2 weeks | Naked | 6 | 5258 ± 363 | 2901 ± 242 | 55.5 ± 4.2 |
| | Encapsulated | 7 | 4640 ± 450 | 4530 ± 616 | 97.5 ± 8.0 |
| 3 weeks | Naked | 4 | 5066 ± 650 | 1408 ± 789 | 24.1 ± 10.3 |
| | Encapsulated | 4 | 5101 ± 563 | 3600 ± 509 | 71.5 ± 7.6 |

*mean ± SEM

TABLE 8

Encapsulated and Naked Canine Islets Transplanted to Diabetic Nude Mice After Long Term Culture

| Group | n | Tx Dose (IE) | Tx Site | Graft Survival (days) | Success (%) >60 days Survival |
|---|---|---|---|---|---|
| 1 week | | | | | |
| Encap. | 4 | 1000 | IP | 127*, 170*, 185*, 220* | 100 |
| | 6 | 2000 | IP | 100*, 127*, 170*, 198x2*, 255 | 100 |
| Naked | 3 | 2000 | Kidney | 0, 127x2* | 66 |
| 2 weeks | | | | | |
| Encap. | 4 | 1000 | IP | 24, 198x2*, 87 | 75 |
| | 3 | 2000 | IP | 80x2*, 185 | 100 |
| Naked | 3 | 2000 | Kidney | 9, 80x2* | 66 |
| 3 weeks | | | | | |
| Encap. | 3 | 1000 | IP | 178*, 190x2* | 100 |
| | 2 | 2000 | IP | 190*, 248* | 100 |
| Naked | 3 | 2000 | Kidney | 0, 23, >273 | 33 |

> = still ongoing
* = graft recovered or animal dead when normoglycemic.

The above is a detailed description of particular embodiments of the invention. It is recognized that departures from the disclosed embodiment may be made within the scope of the invention and that obvious modifications will occur to a person skilled in the art. The full scope of the invention is set out in the claims that follow and their equivalents. Accordingly, the claims and specification should not be construed to unduly narrow the full scope of protection to which the invention is entitled.

The references, patents and patent documents cited above are herein incorporated by reference.

What is claimed is:

1. A method for bulk cryopreservation of encapsulated islets comprising the steps of:

(a) providing a flexible container with a capacity of about 50 mL to about 500 mL which contains a bulk solution of encapsulated islets and cryoprotectant;

(b) reducing the temperature of the encapsulated islets to below −100° C.; and (c) maintaining essentially uniform heat transfer from all regions of the encapsulated islets throughout step (b), wherein the container thickness during step (b) is maintained at about 5 mm.

2. The method of claim 1 wherein the configuration of the container is maintained essentially constant throughout step (b).

3. The method of claim 1 wherein the cross-sectional area of the container during step (b) is maintained essentially constant along substantially the entire length of the container.

4. The method of claim 1 wherein step (a) comprises providing the encapsulated islets in a container having a capacity of about 50 mL.

5. A method for bulk cryopreservation of encapsulated islets comprising the steps of:

(a) providing a flexible container with a capacity of about 50 mL to about 500 mL which contains a bulk solution of encapsulated islets and cryoprotectant;

(b) supercooling the encapsulated islets to a temperature below the freezing point of the solution;

(c) after step (b), freezing essentially all of the encapsulated islets by nucleation;

(d) after step (c), further reducing the temperature of the encapsulated islets at a controlled rate to below −40° C.; and (e) maintaining essentially uniform heat transfer from essentially all regions of the encapsulated islets during steps (c) and (d), wherein the container thickness during steps (c) and (d) is maintained at about 5 mm.

6. The method of claim 5 including the step of maintaining the configuration of the container essentially constant as the temperature of the biological material changes.

7. The method of claim 5 including the step of placing the flexible container in a rigid holder that maintains the configuration of the container essentially constant during steps (b), (c) and (d).

8. The method of claim 5 wherein the container thickness during steps (b), (c), and (d) is maintained at about 5 mm.

* * * * *